(12) United States Patent
Kawamura et al.

(10) Patent No.: US 8,399,699 B2
(45) Date of Patent: Mar. 19, 2013

(54) PROCESS FOR PRODUCTION OF ALKOXYCARBONYL COMPOUND

(75) Inventors: Masato Kawamura, Ehime (JP); Michio Yamamoto, Shiga (JP); Fumisato Goto, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 176 days.

(21) Appl. No.: 12/934,163

(22) PCT Filed: Mar. 23, 2009

(86) PCT No.: PCT/JP2009/055670
§ 371 (c)(1),
(2), (4) Date: Sep. 23, 2010

(87) PCT Pub. No.: WO2009/119508
PCT Pub. Date: Oct. 1, 2009

(65) Prior Publication Data
US 2011/0046417 A1   Feb. 24, 2011

(30) Foreign Application Priority Data

Mar. 25, 2008 (JP) ................................. 2008-077980
Oct. 20, 2008 (JP) ................................. 2008-269412

(51) Int. Cl.
*C07C 67/36* (2006.01)
(52) U.S. Cl. ..................................... 560/207
(58) Field of Classification Search .................. 560/207; 568/579
See application file for complete search history.

(56) References Cited

U.S. PATENT DOCUMENTS

| 5,081,286 A | * | 1/1992 | Doyle et al. | 560/206 |
| 5,869,738 A | * | 2/1999 | Pan et al. | 560/207 |
| 5,908,958 A | * | 6/1999 | Drent et al. | 560/207 |

FOREIGN PATENT DOCUMENTS

| JP | 2277551 A | 11/1990 |
| JP | 2290831 A | 11/1990 |
| JP | 4215851 A | 8/1992 |
| JP | 5194317 A | 8/1993 |
| JP | 5221923 A | 8/1993 |
| JP | 9501671 T | 2/1997 |
| JP | 2002504093 T | 2/2002 |
| WO | WO-95/05357 A1 | 2/1995 |
| WO | WO-2007114457 A1 | 10/2007 |

OTHER PUBLICATIONS

PCT/JP2009/055670 International Search Report (mailed Jun. 2, 2009) (2 pages).
Supplementary European Search Report and Written Opinion for corresponding European Patent Application No. 09724353 mailed on Jan. 6, 2012 (5 pages).

* cited by examiner

*Primary Examiner* — Sikarl Witherspoon
(74) *Attorney, Agent, or Firm* — Wilmer Cutler Pickering Hale and Dorr LLP

(57) ABSTRACT

A method for producing an alkoxycarbonyl compound wherein the method comprises reacting carbon monoxide and an alcohol compound with methylacetylene in the presence of a catalyst containing a Group 10 metal compound, a proton acid and a phosphine compound, the propadiene content of the methylacetylene is 50 ppm or less, the phosphine compound is used at greater than 0.000020 mol with respect to 1 mol of methylacetylene, and the carbon monoxide and the alcohol compound are reacted with 200000 mol or more of methylacetylene with respect to 1 mol of the Group 10 metal compound.

17 Claims, No Drawings

PROCESS FOR PRODUCTION OF ALKOXYCARBONYL COMPOUND

TECHNICAL FIELD

The present invention relates to a method for producing an alkoxycarbonyl compound.

BACKGROUND ART

Patent documents 1, 2 and 3 disclose processes for production of methyl methacrylate by reaction of methylacetylene with carbon monoxide and methanol, using palladium compounds, proton acids and phosphine compounds as catalysts. The methylacetylene used in such reactions is known to contain propadiene in a range of 0.2%-3%.
[Patent document 1] JP No. H02-277551 A
[Patent document 2] JP No. H09-501671 T
[Patent document 3] JP No. H02-290831 A

DISCLOSURE OF THE INVENTION

Conventional processes for production of alkoxycarbonyl compounds have poor productivity per unit of palladium metal, and the efficiency, in terms of a reaction using a precious metal catalyst, has not always been satisfactory from an industrial viewpoint.

The present invention provides an efficient process for production of an alkoxycarbonyl compound.

Specifically, the invention relates to a method for producing an alkoxycarbonyl compound wherein the method comprises reacting carbon monoxide and an alcohol compound with methylacetylene in the presence of a catalyst containing a Group 10 metal compound, a proton acid and a phosphine compound, the propadiene content of the methylacetylene is 50 ppm or less, the phosphine compound is used at greater than 0.000020 mol with respect to 1 mol of methylacetylene, and the carbon monoxide and the alcohol compound are reacted with 200000 mol or more of methylacetylene with respect to 1 mol of the Group 10 metal compound.

According to the invention it is possible to produce alkoxycarbonyl compounds in an efficient manner.

BEST MODES FOR CARRYING OUT THE INVENTION

The methylacetylene used for the process of the invention has a propadiene content of 50 ppm or less, preferably 30 ppm or less, more preferably 20 ppm or less, yet more preferably 10 ppm or less and most preferably 5 ppm or less. The methylacetylene may also contain impurities in addition to propadiene so long as they do not significantly inhibit alkoxycarbonylation. As such impurities there may be mentioned, specifically, butadiene, propylene, butene, propane, carbon monoxide and carbon dioxide. The carbon monoxide used for the invention may be pure carbon monoxide, or it may contain a gas inert to the catalyst and methylacetylene such as nitrogen, helium, carbon dioxide or argon.

The reaction of the invention is conducted using a Group 10 metal compound, a proton acid and a phosphine compound as the catalyst. The catalyst is ordinarily used as a mixture of the Group 10 metal compound, proton acid and phosphine compound. The amounts of Group 10 metal compound, proton acid and phosphine compound used may be catalytic amounts, and they are typically used in the following forms.

As Group 10 metal compounds there may be mentioned nickel compounds, palladium compounds and platinum compounds, and preferably palladium compounds. As palladium compounds there may be mentioned palladium acetylacetonate, tetrakis(triphenylphosphine)palladium, bis(triphenylphosphine)palladium acetate, palladium acetate, palladium trifluoroacetate, palladium trifluoromethanesulfonate, palladium sulfate, palladium chloride, and mixtures thereof. More preferred as palladium compounds are palladium acetylacetonate, tetrakis(triphenylphosphine)palladium, bis(triphenylphosphine)palladium acetate, palladium acetate, palladium trifluoroacetate, palladium trifluoromethanesulfonate, palladium sulfate and mixtures thereof, with palladium acetate being even more preferred. The Group 10 metal compound is used in an amount of up to 1/200000 mol, and preferably in the range of 1/1000000-1/200000 mol, with respect to 1 mol of methylacetylene. That is, the methylacetylene is used in the amount of 200000 mol or greater and preferably in the range of 200000-1,000000 mol with respect to 1 mol of the Group 10 metal compound.

There are no particular restrictions on the phosphine compound, but usually a tertiary phosphine compound is used, and preferably it includes an aromatic tertiary phosphine compound represented by the following formula (1).

[Chemical Formula 1]

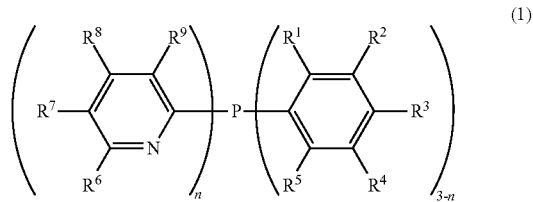

In formula (1), $R^1$, $R^2$, $R^3$, $R^4$, $R^5$, $R^6$, $R^7$, $R^8$ and $R^9$ each independently represent a substituent selected from the group consisting of hydrogen, halogen atoms, cyano, hydroxyl, alkyl groups optionally substituted with halogen atoms, aralkyl, substituted or unsubstituted aryl, pyridyl, silyl, amino, alkoxy, aralkyloxy, aryloxy and acyl, with the adjacent groups optionally bonding together to form rings. The letter n represents an integer of 0-3.

More preferred phosphine compounds are aromatic tertiary pyridylphosphine compounds wherein the integer n in general formula (1) is 1 or greater. Specific examples of aromatic tertiary pyridylphosphine compounds include diphenyl(2-pyridyl)phosphine, diphenyl(6-methyl-2-pyridyl)phosphine, diphenyl(6-ethyl-2-pyridyl)phosphine, diphenyl[6-(n-propyl)-2-pyridyl]phosphine, diphenyl[6-(iso-propyl)-2-pyridyl]phosphine, diphenyl[6-(n-butyl)-2-pyridyl]phosphine, diphenyl[6-(iso-butyl)-2-pyridyl]phosphine, diphenyl(6-phenyl-2-pyridyl)phosphine, diphenyl(6-hydroxy-2-pyridyl)phosphine, diphenyl(6-methoxy-2-pyridyl)phosphine, diphenyl(6-fluoro-2-pyridyl)phosphine, diphenyl(6-chloro-2-pyridyl)phosphine, diphenyl(6-bromo-2-pyridyl)phosphine, bis(4-fluorophenyl)(2-pyridyl)phosphine, bis(4-chlorophenyl)(2-pyridyl)phosphine, bis(4-bromophenyl)(2-pyridyl)phosphine, bis(3-methylphenyl)(2-pyridyl)phosphine, bis(4-methylphenyl)(2-pyridyl)phosphine, bis(4-methoxyphenyl)(2-pyridyl)phosphine, bis[4-(trifluoromethyl)phenyl](2-pyridyl)phosphine, bis(3,4,5-trifluorophenyl)(2-pyridyl)phosphine, bis(4-fluorophenyl)(6-methyl-2-pyridyl)phosphine, bis(4-chlorophenyl)(6-methyl-2-pyridyl)phosphine, bis(4-bromophenyl)(6-methyl-2-pyridyl)phosphine, bis(3-methylphenyl)(6-methyl-2-pyridyl)phosphine, bis(4-methylphenyl)(6-methyl-2- pyridyl)phosphine, bis(4-methoxyphenyl)(6-methyl-2-pyridyl)phosphine, bis[4-(trifluoromethyl)phenyl](6-methyl-2-pyridyl)phosphine, bis(4-methylphenyl)(6-ethyl-2-pyridyl)phosphine, bis(4-methylphenyl)[6-(n-propyl)-2-pyridyl]phosphine, bis(4-methylphenyl)[6-(iso-propyl)-2-pyridyl]phosphine, bis(4-methylphenyl)[6-(n-butyl)-2-pyridyl]phosphine, bis(4-methylphenyl) [6-(iso-butyl)-2-pyridyl]phosphine, bis(4-methoxyphenyl)(6-ethyl-2-pyridyl)phosphine, bis(4-methoxyphenyl)[6-(n-propyl)-2-pyridyl]phosphine, bis(4-methoxyphenyl)[6-(iso-propyl)-2-pyridyl]phosphine, bis(4-methoxyphenyl)[6-(n-butyl)-2-pyridyl]phosphine, bis(4-methoxyphenyl)[6-(iso-butyl)-2-pyridyl]phosphine, bis(2-pyridyl)phenylphosphine, tris(2-pyridyl)phosphine, bis(6-methyl-2-pyridyl)phenylphosphine and tris(6-methyl-2-pyridyl)phosphine, and even more preferred examples are diphenyl(2-pyridyl)phosphine, diphenyl(6-methyl-2-pyridyl)phosphine and bis(4-methylphenyl)(6-methyl-2-pyridyl)phosphine.

These aromatic tertiary pyridylphosphine compounds are limited to being used alone, and may be used in appropriate combinations. The amount of aromatic tertiary pyridylphosphine compound used is not particularly restricted so long as it is greater than 0.000020 mol with respect to 1 mol of methylacetylene, but it is preferably both greater than 0.000020 mol with respect to 1 mol of methylacetylene and 2 mol or more with respect to 1 mol of propadiene, and yet more preferably greater than 0.000020 mol and 0.00048 mol or less with respect to 1 mol of methylacetylene and 2 mol or more with respect to 1 mol of propadiene.

The aromatic tertiary pyridylphosphine compound may be produced by a known process. Different types of aromatic tertiary pyridylphosphine compounds can be produced by reacting halogenated pyridines with alkyllithiums for lithiation and then reacting the products with phosphine chloride, as disclosed in JP No. H02-277551 A, for example.

Favorable results are also obtained when a monodentate tertiary monophosphine compound is used with an aromatic tertiary pyridylphosphine compound. A monodentate tertiary monophosphine compound in this case is a tertiary phosphine compound that contains no functional groups capable of serving as coordination sites other than a single phosphorus atom. Examples of monodentate tertiary monophosphine compounds include trialkylphosphine compounds, and aromatic tertiary phosphine compounds having identical or different aryl groups optionally substituted with one or more substituents selected from the group consisting of alkyl, halogen atoms, haloalkyl and alkoxy groups. Specific examples of monodentate tertiary monophosphine compounds include triethylphosphine, tributylphosphine, tricyclohexylphosphine, triphenylphosphine, tris(4-fluorophenyl)phosphine, tris(4-chlorophenyl)phosphine, tris(4-methylphenyl)phosphine, tris[4-(trifluoromethyl)phenyl]phosphine, tris(4-methoxyphenyl)phosphine, tris(3-methylphenyl)phosphine, tris[3,5-bis(trifluoromethyl)phenyl]phosphine, (4-methylphenyl)(diphenyl)phosphine, and mixtures thereof, preferred among which are the aforementioned aromatic tertiary phosphine compounds, and even more preferably triphenylphosphine. There are no particular restrictions on its amount of use, and it may be in the range of 1-600 mol and more preferably 1-300 mol with respect to 1 mol of the Group 10 metal compound.

Examples of proton acids include organic and inorganic proton acids. Examples of specific proton acids include boric acid, orthophosphoric acid, pyrophosphoric acid, sulfuric acid, hydrohalic acids, benzenephosphoric acid, benzenesulfonic acid, p-toluenesulfonic acid, naphthalenesulfonic acid, chlorosulfonic acid, methanesulfonic acid, trifluoromethanesulfonic acid, trimethylmethanesulfonic acid, monochloroacetic acid, dichloroacetic acid, trichloroacetic acid, trifluoroacetic acid, oxalic acid, bis(trifluoromethanesulfonyl)imide, tris(trifluoromethanesulfonyl)methide, and mixtures thereof, preferred among which are sulfonic acid compounds, and even more preferably methanesulfonic acid. There are no particular restrictions on its amount of use, but 3-300 mol is sufficient, and 10-240 mol is more preferred, with respect to 1 mol of the Group 10 metal compound.

The use of an amine compound as a catalyst in the reaction of the invention is not absolutely essential, but the reaction in the copresence of an amine compound may provide favorable results. The amine compound is not particularly restricted, but normally a known tertiary amine or cyclic amine is used. Specific examples of amine compounds include N,N-dialkylanilines, pyridine, quinoline, isoquinoline, triazine, imidazole, triethylamine, tributylamine, N,N-diisopropylethylamine, and mixtures thereof, with N,N-dimethylaniline and pyridine being preferred. The amount of amine compound added is not particularly restricted, but it is preferably in a range of 1-50 mol and more preferably 1-10 mol with respect to 1 mol of the proton acid.

The alcohol compound used for the invention is also not particularly restricted, and specifically there may be mentioned methanol, ethanol, 1-propanol, 2-propanol, 1-butanol, sec-butanol, tert-butanol and ethylene glycol. According to a preferred mode, methanol may be reacted to produce methyl methacrylate. The amount of alcohol compound used is not particularly restricted, but preferably it is 1 mol or more with respect to 1 mol of methylacetylene.

The use of a solvent in the reaction of the invention is not absolutely essential, but from the viewpoint of safety the methylacetylene/propadiene partial pressure is preferably lowered, and the excess alcohol may be suitably used instead of a solvent. However, a separate solvent may also be used. There are no particular restrictions on usable solvents so long as the alkoxycarbonylation reaction is not significantly inhibited, and there may be mentioned aromatic hydrocarbons, aliphatic hydrocarbons, sulfoxides, sulfones, esters, ketones, ethers, amides, alcohols, ionic fluids, and mixtures of the foregoing. There are no particular restrictions on their amounts of use. Specific examples of solvents include toluene, xylene, hexane, cyclohexane, heptane, octane, dimethyl sulfoxide, sulfolane, methyl acetate, ethyl acetate, methyl acrylate, ethyl acrylate, methyl methacrylate, ethyl methacrylate, acetone, methyl ethyl ketone, anisole, dimethoxyethane, diethyl ether, tetrahydrofuran, diglyme, dibutyl ether, dimethylformamide, N-methylpyrrolidone, dimethylacetamide, methanol, ethanol, propanol, butanol, ethylene glycol, and mixtures thereof.

The reaction temperature in the method for alkoxycarbonylation of methylacetylene according to the invention is not particularly restricted, but it is preferably in the range of 20-100° C. The reaction time depends on the amount of catalyst used and on the reaction temperature and pressure, but it is usually 0.5-48 hours. There are no particular restrictions on the reaction pressure for the alkoxycarbonylation of methylacetylene, but it is preferably 0.5-10 MPaG (gauge pressure) and even more preferably 1-7 MPaG (gauge pressure). The carbon monoxide partial pressure is also not particularly restricted, but is preferably 0.5-10 MPaG (gauge pressure) and even more preferably 1-7 MPaG (gauge pressure). The mode of reaction for the invention is not restricted and may be, for example, a batch system or continuous system.

The alkoxycarbonyl compound obtained by alkoxycarbonylation of methylacetylene may be, specifically, an alkyl methacrylate compound.

EXAMPLES

The present invention is now explained in greater detail through the following examples, with the understanding that these examples are not limitative on the invention.

Production Example 1

In a nitrogen-substituted 1000 ml Schlenk flask there were dissolved 125 mg (0.550 mmol) of palladium acetate and 1.49 g (5.50 mmol) of diphenyl(2-pyridyl)phosphine in 750 ml of methanol, and then 535 µl (8.25 mmol) of methanesulfonic acid was added and the mixture was stirred at room temperature to obtain a catalyst solution. The obtained catalyst solution was introduced into a nitrogen-substituted 1500 ml autoclave and cooled with a dry ice-ethanol bath. In the cooled autoclave there was introduced 203 g of commercially available methylacetylene (5.01 mol, propadiene content: 3500-3000 ppm), and the mixture was pressurized with carbon monoxide and held at 1.2 MPa. (During the reaction, the amount of consumed carbon monoxide was constantly re-introduced through a pressure reducing valve for a total pressure of 1.2 MPa.) After stirring at 50° C. for 3 hours, the liquid was again cooled with a dry ice-ethanol bath. After removing the unreacted carbon monoxide, it was heated to 35° C. and the gasified methylacetylene gas was collected as liquid in a Schlenk flask that had been pre-cooled in a dry ice-ethanol bath, and it was filled directly into a cylinder to obtain 99.3 g (49%) methylacetylene with a propadiene content of 802 ppm.

Production Example 2

The same procedure was followed as in Production Example 1, except that 33.8 g (835 mmol) of the methylacetylene obtained in Production Example 1 was used instead of commercially available methylacetylene, with 15.0 mg (0.0660 mmol) of palladium acetate, 179 mg (0.660 mmol) of diphenyl(2-pyridyl)phosphine, 128 µl (1.98 mmol) of methanesulfonic acid and 20 ml of methanol, a 100 ml autoclave was used as the reactor, and the reaction pressure was kept at 2.0 MPa. As a result there was obtained 10.7 g (32%) of methylacetylene with a propadiene content of 37 ppm.

Production Example 3

After dissolving 2-bromo-6-methylpyridine (23.5 mmol) in 40 ml of tetrahydrofuran, the mixture was cooled in a dry ice-ethanol bath, 1.59 M hexane solution of n-butyllithium (23.5 mmol) was added dropwise while stirring, and stirring was continued for 10 minutes to obtain a reaction mixture. To the obtained reaction mixture there was added chlorobis(4-methylphenyl)phosphine (17.5 mmol) dissolved in 40 ml of tetrahydrofuran, and stirring was continued at room temperature for 2 hours. The reaction solution was quenched with water and extracted with ethyl acetate, and the organic layer was dried over anhydrous magnesium sulfate. After distilling off the solvent under reduced pressure, purification was performed twice by silica gel column chromatography (developing solution: hexane/ethyl acetate=5/1, 9/1), to obtain 2.68 g of bis(4-methylphenyl)(6-methyl-2-pyridyl)phosphine (50% yield).

$^1$H-NMR (CDCl$_3$, 270 Hz): δ 7.41 (1H, td, J=8.2 Hz), 7.29-7.10 (8H, m), 7.00 (1H, d, J=8 Hz), 6.81 (1H, d, J=8 Hz), 2.56 (3H, s), 2.34 (6H, s)

Example 1

In a Schlenk flask there were dissolved 1.8 mg (0.0080 mmol) of palladium acetate and 130 mg (0.480 mmol) of diphenyl(2-pyridyl)phosphine in 45 mL of methanol, and then 0.15 ml (1.20 mmol) of N,N-dimethylaniline and 47 µl (0.72 mmol) of methanesulfonic acid were added to prepare a catalyst solution. After separating off 1.7 ml of the catalyst solution (corresponding to 0.00030 mmol of palladium), it was introduced into a stainless steel autoclave with a 100 ml internal volume under a nitrogen atmosphere, and then 28.3 ml of methanol was further introduced therein. An autoclave containing the catalyst solution was cooled in a dry ice-ethanol bath, and after introducing 6.87 g (170 mmol) of methylacetylene with a propadiene concentration of less than 3 ppm, the mixture was pressurized with carbon monoxide (CO) and held at 5 MPaG. In order to maintain a CO partial pressure of 5 MPaG during the reaction, the amount of consumed carbon monoxide was constantly re-introduced through a pressure reducing valve. When the reaction liquid that had been kept at a reaction temperature of 65° C. for 7 hours was subjected to quantitative analysis by gas chromatography (GC), the amount of methyl methacrylate production was $5.1 \times 10^5$ mol/mol Pd and the selectivity for recovered product was 95%.

Example 2

In a Schlenk flask there were dissolved 1.8 mg (0.0080 mmol) of palladium acetate and 521 mg (1.92 mmol) of diphenyl(2-pyridyl)phosphine in 45 mL of methanol, and then 0.62 ml (4.80 mmol) of N,N-dimethylaniline and 187 µl (2.88 mmol) of methanesulfonic acid were added to prepare a catalyst solution. After separating off 1.7 ml of the catalyst solution (corresponding to 0.00030 mmol of palladium), it was introduced into a stainless steel autoclave with a 100 ml internal volume under a nitrogen atmosphere, and then 28.3 ml of methanol was further introduced therein. An autoclave containing the catalyst solution was cooled in a dry ice-ethanol bath, and after introducing 6.67 g (165 mmol) of methylacetylene with a propadiene concentration of 24 ppm, the mixture was pressurized with carbon monoxide and held at 5 MPaG. In order to maintain a CO partial pressure of 5 MPaG during the reaction, the amount of consumed carbon monoxide was constantly re-introduced through a pressure reducing valve. When the reaction liquid that had been kept at a reaction temperature of 65° C. for 6 hours was subjected to quantitative analysis by gas chromatography (GC), the amount of methyl methacrylate production was $5.2 \times 10^5$ mol/mol Pd and the selectivity for recovered product was 96%.

Example 3

In a Schlenk flask there were dissolved 1.8 mg (0.0080 mmol) of palladium acetate and 90.5 mg (0.32 mmol) of (6-methyl-2-pyridyl)diphenylphosphine in 45 mL of methanol, and then 0.10 ml (0.80 mmol) of N,N-dimethylaniline and 31 µl (0.48 mmol) of methanesulfonic acid were added to prepare a catalyst solution. After separating off 1.7 ml of the catalyst solution (corresponding to 0.00030 mmol of palladium), it was introduced into a stainless steel autoclave with a 100 ml internal volume under a nitrogen atmosphere, and then 28.3 ml of methanol was further introduced therein. An autoclave containing the catalyst solution was cooled in a dry ice-ethanol bath, and after introducing 6.29 g (155 mmol) of methylacetylene with a propadiene concentration of less than 10 ppm, the mixture was pressurized with carbon monoxide and held at 5 MPaG. In order to maintain a CO partial pressure of 5 MPaG during the reaction, the amount of consumed carbon monoxide was constantly re-introduced through a pressure reducing valve. When the reaction liquid that had been kept at a reaction temperature of 65° C. for 7 hours was subjected to quantitative analysis by gas chromatography (GC), the amount of methyl methacrylate production was $3.5 \times 10^5$ mol/mol Pd and the selectivity for recovered product was 94%.

Example 4

In a Schlenk flask there were dissolved 1.8 mg (0.0080 mmol) of palladium acetate, 90.5 mg (0.320 mmol) of diphenyl(6-methyl-2-pyridyl)phosphine and 85.6 mg (0.320 mmol) of triphenylphosphine, in 45 mL of methanol, and then 0.20 ml (1.60 mmol) of N,N-dimethylaniline and 62 μl (0.96 mmol) of methanesulfonic acid were added to prepare a catalyst solution. After separating off 1.7 ml of the catalyst solution (corresponding to 0.00030 mmol of palladium), it was introduced into a stainless steel autoclave with a 100 ml internal volume under a nitrogen atmosphere, and then 28.3 ml of methanol was further introduced therein. An autoclave containing the catalyst solution was cooled in a dry ice-ethanol bath, and after introducing 6.60 g (163 mmol) of methylacetylene with a propadiene concentration of 7 ppm, the mixture was pressurized with carbon monoxide (CO) and held at 5 MPaG. In order to maintain a CO partial pressure of 5 MPaG during the reaction, the amount of consumed carbon monoxide was constantly re-introduced through a pressure reducing valve. When the reaction liquid that had been kept at a reaction temperature of 65° C. for 7 hours was subjected to quantitative analysis by gas chromatography (GC), the amount of methyl methacrylate production was $3.8 \times 10^5$ mol/mol Pd and the selectivity for recovered product was 99%.

Example 5

In a Schlenk flask there were dissolved 1.8 mg (0.0080 mmol) of palladium acetate, 86.9 mg (0.320 mmol) of diphenyl(2-pyridyl)phosphine and 96.4 mg (0.360 mmol) of triphenylphosphine, in 45 mL of methanol, and then 0.20 ml (1.60 mmol) of N,N-dimethylaniline and 62 μl (0.96 mmol) of methanesulfonic acid were added to prepare a catalyst solution. After separating off 1.7 ml of the catalyst solution (corresponding to 0.00030 mmol of palladium), it was introduced into a stainless steel autoclave with a 100 ml internal volume under a nitrogen atmosphere, and then 28.3 ml of methanol was further introduced therein. An autoclave containing the catalyst solution was cooled in a dry ice-ethanol bath, and after introducing 6.11 g (151 mmol) of methylacetylene with a propadiene concentration of 4 ppm, the mixture was pressurized with carbon monoxide (CO) and held at 5 MPaG. In order to maintain a CO partial pressure of 5 MPaG during the reaction, the amount of consumed carbon monoxide was constantly re-introduced through a pressure reducing valve. When the reaction liquid that had been kept at a reaction temperature of 65° C. for 7 hours was subjected to quantitative analysis by gas chromatography (GC), the amount of methyl methacrylate production was $3.4 \times 10^5$ mol/mol Pd. The selectivity for the recovered product was 99%.

Example 6

The same procedure was followed as in Example 1 except that in the Schlenk flask there were dissolved 1.8 mg (0.0080 mmol) of palladium acetate and 86.9 mg (0.320 mmol) of diphenyl(2-pyridyl)phosphine in 45 mL of methanol, after which 31 μl (0.48 mmol) of methanesulfonic acid was added to prepare the catalyst solution and 6.30 g (156 mmol) of methylacetylene with a propadiene content of 13 ppm was used; as a result the methyl methacrylate production was $1.5 \times 10^5$ mol/mol Pd and the selectivity for the recovered product was 84%.

Example 7

The same procedure was followed as in Example 3 except that there were used 86.9 mg (0.320 mmol) of diphenyl(2-pyridyl)phosphine as the phosphine compound and 6.25 g (154 mmol) of methylacetylene with a propadiene concentration of 25 ppm, and as a result the methyl methacrylate production was $1.7 \times 10^5$ mol/mol Pd and the selectivity for the recovered product was 81%.

Example 8

The same procedure was followed as in Example 3 except that there were used 98.7 mg (0.32 mmol) of bis(4-methylphenyl)(6-methyl-2-pyridyl)phosphine as the phosphine compound and 6.38 g (158 mmol) of methylacetylene with a propadiene concentration of 11 ppm, and as a result the methyl methacrylate production was $2.5 \times 10^5$ mol/mol Pd. The selectivity for the recovered product was 97%.

Reference Example 1

The same procedure was followed as in Example 2 except that there was used 6.66 g (165 mmol) of methylacetylene with a propadiene concentration of 537 ppm, and as a result the methyl methacrylate production was reduced to $1.8 \times 10^5$ mol/mol Pd and the selectivity for the recovered product was 81%.

Comparative Example 1

The same procedure was followed as in Example 1 except that in the Schlenk flask there were dissolved 1.8 mg (0.0080 mmol) of palladium acetate and 21.7 mg (0.0800 mmol) of diphenyl(2-pyridyl)phosphine in 45 mL of methanol, after which 26 μl (0.20 mmol) of N,N-dimethylaniline and 8 μl (0.12 mmol) of methanesulfonic acid were added to prepare the catalyst solution, and 6.11 g (151 mmol) of methylacetylene with a propadiene content of 2 ppm was used; as a result the methyl methacrylate production was only $0.01 \times 10^5$ mol/mol Pd.

Comparative Example 2

The same procedure was followed as in Example 7 except that there was used 6.13 g (151 mmol) of methylacetylene with a propadiene concentration of 389 ppm, and as a result the methyl methacrylate production was reduced to $0.26 \times 10^5$ mol/mol Pd.

The results for the examples, reference example and comparative examples are shown in Table 1.

TABLE 1

| | | | Example | | | | | |
|---|---|---|---|---|---|---|---|---|
| | | | 1 | 2 | 3 | 4 | 5 | 6 |
| Catalyst | Group 10 metal compound | Palladium acetate (mmol) | 0.008 | 0.008 | 0.008 | 0.008 | 0.008 | 0.008 |
| | Phosphine compound | Diphenyl(2-pyridyl)phosphine (mmol) | 0.48 | 1.92 | — | — | 0.32 | 0.32 |
| | | (6-Methyl-2-pyridyl) diphenylphosphine (mmol) | — | — | 0.32 | — | — | — |
| | | Diphenyl(6-methyl-2-pyridyl) phosphine (mmol) | — | — | — | 0.32 | — | — |
| | | Bis(4-methylphenyl) (6-methyl-2-pyridyl)phosphine (mmol) | — | — | — | — | — | — |
| | | Triphenylphosphine (mmol) | — | — | — | 0.32 | 0.36 | — |
| | Amine compound | N,N-Dimethylaniline (mmol) | 1.2 | 4.8 | 0.8 | 1.6 | 1.6 | — |
| | Proton acid | Methanesulfonic acid (mmol) | 0.72 | 2.88 | 0.48 | 0.96 | 0.96 | 0.48 |
| Palladium (mmol) | | | 0.0003 | 0.0003 | 0.0003 | 0.0003 | 0.0003 | 0.0003 |
| Methylacetylene (mmol) | | | 170 | 165 | 155 | 163 | 151 | 156 |
| Propadiene concentration (ppm) | | | <3 | 24 | <10 | 7 | 4 | 13 |
| Methylacetylene (mol) (with respect to 1 mol of Group 10 metal compound) | | | $5.7 \times 10^5$ | $5.5 \times 10^5$ | $5.2 \times 10^5$ | $5.4 \times 10^5$ | $5.0 \times 10^5$ | $5.2 \times 10^5$ |
| Phosphine compound (mol) (with respect to 1 mol of methylacetylene) | | | 0.000106 | 0.000436 | 0.000077 | 0.000147 | 0.000169 | 0.000077 |
| Methyl methacrylate production (mol/mol Pd) | | | $5.1 \times 10^5$ | $5.2 \times 10^5$ | $3.5 \times 10^5$ | $3.8 \times 10^5$ | $3.4 \times 10^5$ | $1.5 \times 10^5$ |
| Selectivity (%) | | | 95 | 96 | 94 | 99 | 99 | 84 |

| | | | Example | | Ref. EX | Comp. EX | |
|---|---|---|---|---|---|---|---|
| | | | 7 | 8 | 1 | 1 | 2 |
| Catalyst | Group 10 metal compound | Palladium acetate (mmol) | 0.008 | 0.008 | 0.008 | 0.008 | 0.008 |
| | Phosphine compound | Diphenyl(2-pyridyl)phosphine (mmol) | 0.32 | — | 1.92 | 0.08 | 0.32 |
| | | (6-Methyl-2-pyridyl) diphenylphosphine (mmol) | — | — | — | — | — |
| | | Diphenyl(6-methyl-2-pyridyl) phosphine (mmol) | — | — | — | — | — |
| | | Bis(4-methylphenyl) (6-methyl-2-pyridyl)phosphine (mmol) | — | 0.32 | — | — | — |
| | | Triphenylphosphine (mmol) | — | — | — | — | — |
| | Amine compound | N,N-Dimethylaniline (mmol) | 0.8 | 0.8 | 4.8 | 0.2 | 0.8 |
| | Proton acid | Methanesulfonic acid (mmol) | 0.48 | 0.48 | 2.88 | 0.12 | 0.48 |
| Palladium (mmol) | | | 0.0003 | 0.0003 | 0.0003 | 0.0003 | 0.0003 |
| Methylacetylene (mmol) | | | 154 | 158 | 165 | 151 | 151 |
| Propadiene concentration (ppm) | | | 25 | 11 | 537 | 2 | 389 |
| Methylacetylene (mol) (with respect to 1 mol of Group 10 metal compound) | | | $5.1 \times 10^5$ | $5.3 \times 10^5$ | $5.5 \times 10^5$ | $5.0 \times 10^5$ | $5.0 \times 10^5$ |
| Phosphine compound (mol) (with respect to 1 mol of methylacetylene) | | | 0.000078 | 0.000076 | 0.000436 | 0.000020 | 0.000079 |
| Methyl methacrylate production (mol/mol Pd) | | | $1.7 \times 10^5$ | $2.5 \times 10^5$ | $1.8 \times 10^5$ | $0.01 \times 10^5$ | $0.26 \times 10^5$ |
| Selectivity (%) | | | 81 | 97 | 81 | — | — |

INDUSTRIAL APPLICABILITY

The present invention is a production method of an alkoxycarbonyl compound, and specifically it may be used for production of alkyl methacrylates, and especially methyl methacrylate.

The invention claimed is:

1. A method for producing an alkoxycarbonyl compound wherein the method comprises reacting carbon monoxide and an alcohol compound with methylacetylene in the presence of a catalyst containing a Group 10 metal compound, a proton acid and a phosphine compound, the propadiene content of the methylacetylene is 50 ppm or less, the phosphine compound is used at greater than 0.000020 mol with respect to 1 mol of methylacetylene, and the carbon monoxide and the alcohol compound are reacted with 200000 mol or more of methylacetylene with respect to 1 mol of the Group 10 metal compound.

2. The method according to claim 1, wherein the catalyst further contains an amine compound.

3. The method according to claim 1, wherein the phosphine compound is used at 2 mol or greater with respect to 1 mol of propadiene.

4. The method according to claim 1, wherein the propadiene content of the methylacetylene is 30 ppm or less.

5. The method according to claim 1, wherein the propadiene content of the methylacetylene is 20 ppm or less.

6. The method according to claim 1, wherein the propadiene content of the methylacetylene is 10 ppm or less.

7. The method according to claim 1, wherein the propadiene content of the methylacetylene is 5 ppm or less.

8. The method according to claim 1, wherein the Group 10 metal compound is a palladium compound.

9. The method according to claim 1, wherein the phosphine compound contains an aromatic tertiary pyridylphosphine.

10. The method according to claim 1, wherein the phosphine compound contains diphenyl(2-pyridyl)phosphine.

11. The method according to claim 1, wherein the phosphine compound contains diphenyl(6-methyl-2-pyridyl)phosphine.

12. The method according to claim 1, wherein the phosphine compound contains bis(4-methylphenyl)(6-methyl-2-pyridyl)phosphine.

13. The method according to claim 9, wherein the phosphine compound further contains a monodentate tertiary monophosphine.

14. The method according to claim 13, wherein the monodentate tertiary monophosphine is triphenylphosphine.

15. The method according to claim 1, wherein the proton acid is a sulfonic acid compound.

16. The method according to claim 2, wherein the amine compound is N,N-dimethylaniline.

17. The method according to claim 2, wherein the phosphine compound is used at 2 mol or greater with respect to 1 mol of propadiene.

* * * * *

UNITED STATES PATENT AND TRADEMARK OFFICE
CERTIFICATE OF CORRECTION

PATENT NO. : 8,399,699 B2  Page 1 of 1
APPLICATION NO. : 12/934163
DATED : March 19, 2013
INVENTOR(S) : Kawamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 174 days.

Signed and Sealed this

First Day of September, 2015

Michelle K. Lee
*Director of the United States Patent and Trademark Office*